(12) United States Patent
John et al.

(10) Patent No.: US 9,357,965 B2
(45) Date of Patent: Jun. 7, 2016

(54) SYSTEM AND METHOD FOR GUIDANCE OF ANESTHESIA, ANALGESIA AND AMNESIA

(71) Applicants: New York University, New York, NY (US); Leslie S. Prichep, Mamaroneck, NY (US)

(72) Inventors: Erwin R. John, Mamaroneck, NY (US); Leslie S. Prichep, Mamaroneck, NY (US)

(73) Assignee: NEW YORK UNIVERSITY, New York, NY (US)

( * ) Notice: Subject to any disclaimer, the term of this patent is extended or adjusted under 35 U.S.C. 154(b) by 139 days.

(21) Appl. No.: 13/735,628

(22) Filed: Jan. 7, 2013

(65) Prior Publication Data

US 2013/0144183 A1 Jun. 6, 2013

Related U.S. Application Data

(63) Continuation of application No. 13/036,730, filed on Feb. 28, 2011, now Pat. No. 8,352,023, which is a continuation of application No. 12/772,659, filed on May 3, 2010, now Pat. No. 7,899,525, which is a continuation of application No. 11/471,122, filed on Jun. 20, 2006, now Pat. No. 7,711,417, which is a continuation of application No. 10/279,131, filed on Oct. 23, 2002, now Pat. No. 7,089,927.

(51) Int. Cl.
| | |
|---|---|
| *A61B 5/04* | (2006.01) |
| *A61B 5/00* | (2006.01) |
| *A61B 5/048* | (2006.01) |
| *A61M 5/172* | (2006.01) |
| *A61M 16/06* | (2006.01) |
| *A61B 5/0484* | (2006.01) |
| *A61M 5/00* | (2006.01) |
| *A61M 16/12* | (2006.01) |
| *A61M 16/18* | (2006.01) |

(52) U.S. Cl.
CPC .............. *A61B 5/4821* (2013.01); *A61B 5/048* (2013.01); *A61B 5/04012* (2013.01); *A61B 5/04845* (2013.01); *A61B 5/4839* (2013.01); *A61M 5/00* (2013.01); *A61M 5/1723* (2013.01); *A61M 16/06* (2013.01); *A61M 16/12* (2013.01); *A61M 16/18* (2013.01); *A61B 5/7225* (2013.01); *A61B 5/7257* (2013.01); *A61M 16/0683* (2013.01); *A61M 2016/0661* (2013.01); *A61M 2202/048* (2013.01); *A61M 2210/0618* (2013.01); *A61M 2230/10* (2013.01)

(58) Field of Classification Search
CPC ..................................................... A61B 5/0476
USPC .................................................. 600/544–545
See application file for complete search history.

(56) References Cited

U.S. PATENT DOCUMENTS

| | | | | |
|---|---|---|---|---|
| 6,016,444 | A * | 1/2000 | John | 600/544 |
| 6,052,619 | A * | 4/2000 | John | 600/544 |
| 2003/0055023 | A1 * | 3/2003 | Rajewski et al. | 514/58 |

*Primary Examiner* — Christian Jang
(74) *Attorney, Agent, or Firm* — Fay Kaplun & Marcin, LLP

(57) ABSTRACT

Method for determining anesthesia dosage includes following steps. First Interventional Agent ("FIA") is administered to Patient at a first rate to achieve First Predetermined Plane of Anesthesia ("FPPA"). Brain waves of Patient are analyzed to formulate First Set of Data ("FSD") corresponding to a self-norm during administration of FIA. First transfer function corresponding to patient biochemical reactions to FIA is computed from FSD. Rate of administration of FIA to Patient is altered by a selected amount after achievement of FPPA for first time required for Patient to deviate from FPPA by predetermined degree. An altered amount of FIA required to cause the predetermined deviation is determined as difference between amount of FIA that would have been delivered to Patient during first time at the first rate and an amount delivered to Patient during the first time at the altered rate. Patient is administered the altered amount of FIA.

13 Claims, 1 Drawing Sheet

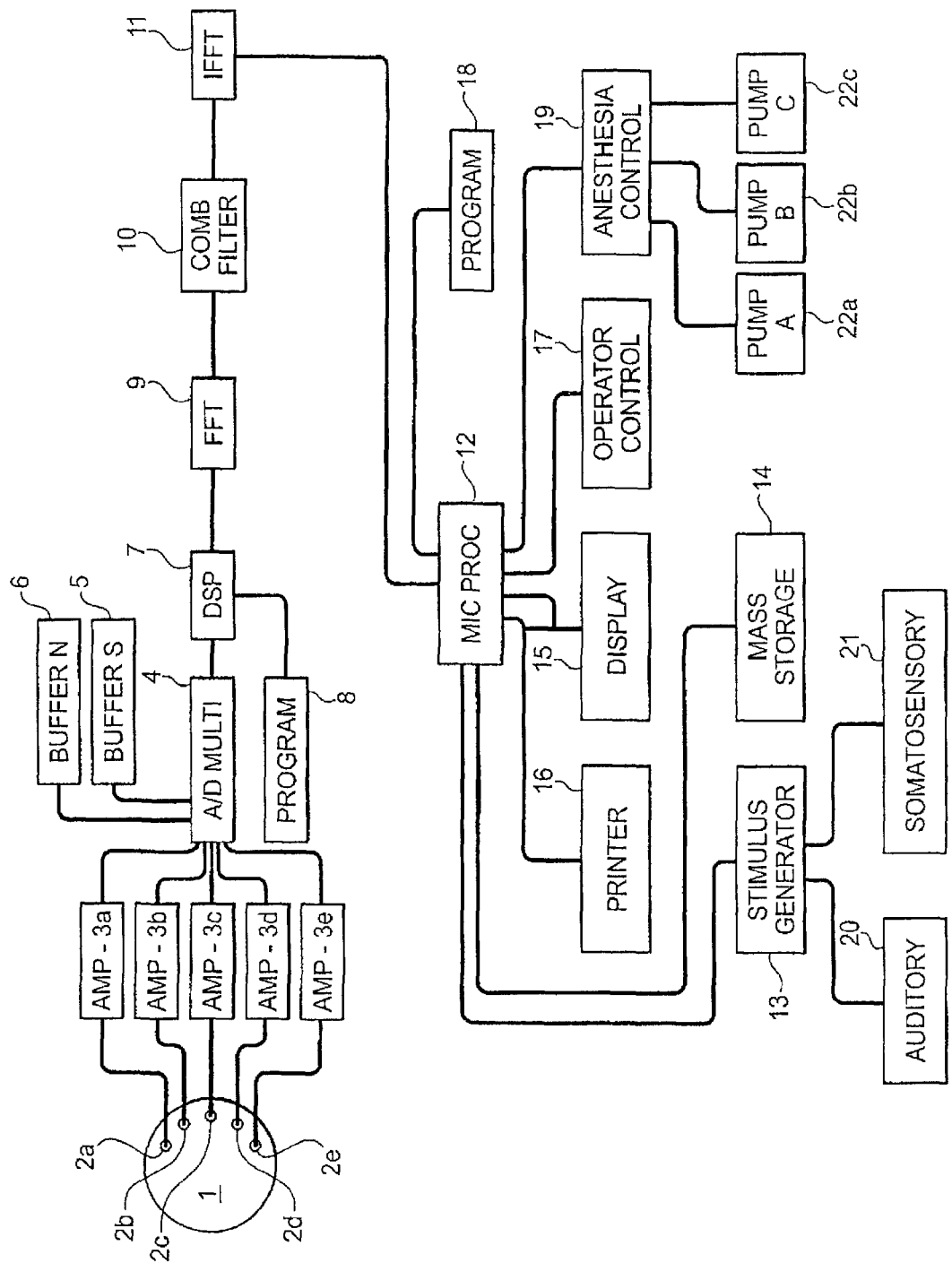

SYSTEM AND METHOD FOR GUIDANCE OF ANESTHESIA, ANALGESIA AND AMNESIA

PRIORITY CLAIM

This application is a Continuation application of U.S. patent application Ser. No. 13/036,730 filed on Feb. 28, 2011, now U.S. Pat. No. 8,352,023; which is a Continuation of U.S. patent application Ser. No. 12/772,659 filed on May 3, 2010, now U.S. Pat. No. 7,899,525; which is a Continuation of U.S. patent application Ser. No. 11/471,122 filed on Jun. 20, 2006, now U.S. Pat. No. 7,711,417; which is a Continuation application of U.S. patent application Ser. No. 10/279,131 filed on Oct. 23, 2002, now U.S. Pat. No. 7,089,927, the entire disclosures of these patents/applications are expressly incorporated herein by reference.

FIELD OF THE INVENTION

The present invention relates to medical systems and methods and more particularly, to an electroencephalograph ("EEG") based system for monitoring or automatic guidance of anesthesia, analgesia, and amnesia during surgical operations.

BACKGROUND INFORMATION

Anesthetic drugs which, when properly administered, induce loss of awareness, are often used for painful and serious medical procedures such as surgical operations. A general anesthetic, when properly administered, will cause a progressive depression of the central nervous system so that the patient loses consciousness. A local anesthetic, however, only affects sensation at the region to which it is applied.

Generally, the patient, prior to a surgical operation, is anesthetized by a specialized medical practitioner ("anesthesiologist") who may be a Board Certified physician, or a specially trained nurse anesthetist. One or more volatile inhalational liquids or gases may be administered (e.g., nitrous oxide, methoxy flurane, sevoflurane, isoflurane, desflurane, ethylene, cyclopropane, ether chloroform, halothane, etc.). Certain desirable anesthetic gases such as Ciboflorane® (Abbott Lab) may sometimes not be used because of their cost. Alternatively, nonvolatile drugs may be administered by injection or intravenous infusion (e.g., flumazenil, thiopentone, Retamine, remifentanyl, midazolam, pentothal, propofol, evipal procaine and Etomidate® (Abbott)). The objectives of general anesthesia administered prior to a surgical operation, may include:

a) blocking the patient's movements and relaxing the patient's muscles to prevent involuntary reflex muscle movements which may interfere with the operation;
b) preventing the patient from being aware (i.e., loss of consciousness, or sedation) during the operation;
c) preventing the patient feeling pain (i.e., loss of sensation, or analgesia) during the operation; and
d) preventing the patient from remembering intra-operative events or discussions (i.e., amnesia).

Furthermore, the anesthesia should not lower blood pressure to a dangerous extent (e.g., below 50 mm Hg for mean arterial pressure (MAP)).

These objectives of general anesthesia may often be attained by separate administration of hypnotic or sedative, analgesic and amnesic agents, in accordance with the clinical judgment of the managing anesthesiologist evaluating the apparent state of the patient and a variety of vital signs.

In order to monitor the "anesthetic depth" or "plane of anesthesia" of the patient, a skilled anesthesiologist looks at the vital signals of the patient (e.g., breathing, blood pressure, etc.) to determine if more, or less, anesthetic is required. Often he/she looks into the patient's eyes to determine the extent of the dilation of the pupils as an indication of the level (or depth) of the effect of the anesthesia. Complete reliance on the availability, skill and attention of the anesthesiologist presents problems in some situations. In addition, respiration may be artificially controlled (e.g., by a respirator) and/or medications may block or alter useful autonomic signs. In the absence of graded neurological reflexes, the depth of suppression of brain activity related to awareness often may not be accurately gauged. The mute, paralyzed patient cannot report the experience of pain. Furthermore, pain cannot be reliably inferred from vital signs since they may be blocked by the presence of medications. In some operations (e.g., heart surgery), the head is covered so that the patient's eyes cannot be viewed and pupillary dilation is not apparent. No reliable estimate may then be made of the possibility that the patient may be aware of environmental events, experience pain and/or be able to store and retrieve memories about unpleasant experiences. Furthermore, during prolonged operations (e.g., 10 to 15 hours or more), the attention of the anesthesia nurse or anesthesiologist may not be constant.

Also, at times, an anesthesiologist may not be available (e.g., in emergency or battlefield situations). Similarly, in isolated geographic locations, it may be impractical to move a patient requiring an operation to a hospital where an anesthesiologist would be available. However, a physician or surgeon may be able to perform a required operation if there were some way to effectively and safely anesthetize the patient.

U.S. Pat. No. 2,690,178 to Bickford purports to describe an automatic system for applying anesthetic to a patient while monitoring the patient's brain waves to monitor the effects of the anesthetic. Bickford used an integrated potential output of the cortex to judge the efficacy of the anesthetic. (See also, U.S. Pat. Nos. 4,280,494 and 4,533,346 to Cosgrove et al. entitled "System for Automatic Feedback-Controlled Administration of Drugs"). The EEG measure used is an "EEG power response" (i.e., a total power output of the brain). However, the use of the single measure of integrated cortex output as described in the Bickford and Cosgrove patents may not provide a reliable control signal for applying a general anesthetic. Different anesthetics have different impacts on power output and several may actually cause an increase in a power detected by a cortical EEG. Furthermore, in some instances, the nature of the power detected changes depending upon electrode position. In addition, not only do different anesthetics have different effects upon the EEG, but those effects may vary from patient to patient as a consequence of different pre-operative medications and/or different biochemical sensitivities.

The following patents which describe methods and apparatus for monitoring and/or controlling the provision of anesthetic to patients are hereby expressly incorporated by reference: U.S. Pat. No. 6,315,736 to Tsutsumi et al.; U.S. Pat. No. 6,317,627 to Ennen et al; U.S. Pat. No. 6,016,444 to E. R. John; U.S. Pat. No. 5,699,808 to E. R. John; U.S. Pat. No. 5,775,330 to Kangas et al.; U.S. Pat. No. 4,557,270 to E. R. John; U.S. Pat. No. 5,010,891 to Chamoun; and U.S. Pat. No. 4,869,264 to Silberstein.

SUMMARY OF THE INVENTION

The present invention is directed to a method for monitoring anesthetization of a patient undergoing a medical procedure, comprising the steps of (a) removably connecting a set of at least two electroencephalograph ("EEG") electrodes to the scalp of the patient, (b) administering sufficient anesthesia to the patient so that the patient attains a plane of anesthesia selected by an operator and (c) amplifying and digitizing brain waves of the patient after step (b) and before beginning the medical procedure to obtain a first set of digital data in combination with the steps of (d) amplifying and digitizing brain waves of the patient during the medical procedure to provide a second set of digital data, (e) analyzing the first and second sets of digital data in at least one of a time domain and a frequency domain; and (f) computing from the data analysis of step (e) separate trajectories for at least two different indices of an anesthetic state of the patient during the medical procedure, the indices being selected from a group including a Depth Index (DI), a Memory Index (MI) and a Pain Index (PI), wherein the DI corresponds to a depth of anesthesia of the patient, PI corresponds to a sensitivity of the patient to pain and MI corresponds to an ability of the patient to form and store memories.

BRIEF DESCRIPTION OF DRAWINGS

FIG. 1 is a block schematic drawing of an exemplary apparatus according to the present invention.

DETAILED DESCRIPTION

The present invention utilizes electrophysiological methods to provide automatic quantitative evaluation separately for a level of awareness (sedation), a sensitivity to pain and/or an ability to comprehend auditory speech and store memories of intraoperative or environmental events. This information may be provided as a monitor to aid an anesthesiologist in the management of an individual patient or may be used as an input to a servo system which automatically delivers anesthetic, analgesic and amnesic agents to optimize the state of a patient.

In particular, before an operation, the anesthesiologist may attach a plurality of removable EEG electrodes to the scalp of the patient (preferably, two to eight electrodes and more preferably, five electrodes). If five active electrodes are used, they may, for example, be placed at F1, F2, F7 and F8 active positions as would be understood by those skilled in the art. Reference electrodes may then be placed, for example, at FPZ and CZ (vertex) and the cheekbone. In addition, an earpiece insert may be used to apply audio stimulus to the patient, and a finger cot electrode may be used to apply slight electrical shocks as somatosensory stimulus. The anesthesiologist may than administer a selected anesthetic to place the patient at a desired depth of anesthesia using his clinical judgment, based upon the patient's vital signs and clinical experience. At that time, measurements of the patient's EEG, AER (Auditory Evoked Response) and/or SER (Somatosensory Evoked Response) may be automatically made to provide an adequate self-norm (reference or base line). Measures of vital signs such as heart rate, stroke volume, blood pressure, respiration and temperature may also be obtained and monitored from the anesthesiology console. In addition, oxygen saturation may be measured, for example, using an NIR sensor such as "INVOS"® In Vitro Optical Spectroscopy) (Somanetics). A QEEG system, which monitors the electrophysiology of the patient, may then be able to detect changes in the clinical state of the patient (e.g., changes in the depth of anesthesia, sensitivity to pain, or probability of memory storage) before there are clinical or qualitative signs of change (e.g., movement, tachycardia, or increased blood pressure). During the operation, the QEEG system automatically and continually collects on-going EEG and also challenges the patient with regularly repeated periods of stimuli to provide evoked potentials, such as AER and SER. These data are subjected to automatic artifact removal and features selected from the self-norm are continuously analyzed and displayed as three trajectories. In one embodiment of the invention, deviations beyond confidence limits (i.e., a reference band) for any of the trajectories, may automatically control the application of the different agents to achieve or maintain the desired depth of anesthesia. Alternatively, this data may be displayed to the anesthesiologist who may then make judgments based on his experience, etc., as to what measures are required to optimize the anesthesia of the patient.

In accordance with one embodiment of the present invention, a Guidance of Anesthesia, Analgesia and Amnesia System ("GAS") includes an ERG system and automatic quantitative analysis of the EEG ("QEEG") and sensory evoked responses. It serves as an intra-operative multimodal monitor to inform the anesthesiologist of the present state of anesthesia of the patient or, if desired, to automatically administer dosages of one or more agents during an operation to facilitate management of the patient. If an anesthesiologist or intensivist is not available, the system may permit a physician or paramedical personnel to manually or automatically maintain the desired level of anesthesia in a patient.

In contrast to conventional systems, the GAS separately evaluates several dimensions of the state of the patient. In addition to serving as a monitor to aid optimal manual management of the patient, the present method and system enables an automatic control of multiple dimensions of anesthesia. Separate measures quantify indices for the depth of anesthesia (DI), sensitivity to pain (Pain Index or PI) and likelihood of storage of Memory Index (MI).

The first dimensional measure, the Depth Index (DI), relates to a depth of anesthesia. If the patient has attained a satisfactory depth of anesthesia, consciousness has been lost and the patient's muscles are sufficiently relaxed so that involuntary muscle movements do not interfere with the operation. This is an over-all measurement of the depth of anesthesia. An example of an agent primarily directed to attain and maintain general anesthesia level (DI), is propofol ("Diprivan"® by Zeneca Phar). The measurement of the patient's immediate sensitivity to pain is called the "Pain Index" (PI) and an example of an agent primarily directed to controlling PI is remifentanyl (selective mu-opiod with a very short half-life). The measurement of the functional state of the patient's memory is called the "Memory Index" (MI). An example of an agent directed primarily to control MI is midazolam (Versed).

General anesthetics produce a progressive depression of the central nervous system. Generally, they produce an irregular descending paralysis of the central nervous system and suppression of the sensory cortex. The paralysis successively affects the basal ganglia, the cerebellum and the spinal cord; without suppression of the medulla (respiratory and cardiac functions). The sensory input to the cortex is suppressed because the sensory pathway from the brain stem reticular formation and the thalamus is inhibited. The electrical activity of every local brain region as well as interactions among regions is auto-regulated by a complex neuroanatomical homeostatic system, producing an EEG power spectrum which is generally predictable in healthy persons of any age and independent of ethnic background, in the absence of perturbing illnesses or chemical substances. Serial measurements are extremely stable and reproducible within any individual. Anesthetic agents alter the relationships within the homeostatic system, producing certain changes in the power spectrum, which have been shown to be invariant with loss of consciousness caused by any agent but reversible with the return of consciousness. Anesthetics act upon pacemaker oscillator cells which normally regulate the stable spontaneous EEG rhythm, generating a power spectrum with a peak that is generally in the center of the Alpha band (8-12 Hz)) via the nucleus reticularis. This inhibits the thalamus via the neurotransmitter gamma-amino butyric acid and, in effect, closes the sensory gate to the cortex. The pacemaker cells are hyperpolarized by this inhibitory influence of n. reticularis, thereby slowing their oscillations to produce slower Alpha waves and enhancement of Theta waves. The slower Alpha waves and Theta waves, and other distinctive alterations of the patient's normal regional EEG power spectra, and electrophysiological signs of interactions between regions, may be detected by the QEEG analysis system of the present invention. Using pattern recognition algorithms, which may be discriminant functions, quantitative features are continuously extracted from ongoing EEG data and used to construct a scale for depth of anesthesia, the Depth Index (DI). This information may be presented to the anesthesiologist to serve as an adjunct to the manual management of the patient. Alternatively, servo systems may be used to administer appropriate agents automatically to control the DI.

The present invention presents a relatively simple and yet effective and reliable system and method for the monitoring and/or control of the multiple dimensions of anesthesia. The method is based upon computation of the covariance matrix of spectral quantitative EEG (QEEG) features within each electrode and among a set of electrode positions. In its simplest form, it uses a set of anterior (frontal) EEG electrodes on the forehead. When the patient attains the surgical plane of anesthesia, the power in each band will change within each electrode and the cross-spectral matrix will change. One way to display this data may be as a scrolling waterfall of the power spectra from each lead, updated at periodic intervals (e.g., Compressed Spectral Array or "CSA"). The means and standard deviations of baseline samples of the covariance matrices and the measures may be used to define a self-norm. As updated samples of EEG are analyzed, a comparison relative to population or self-normative data is made of the absolute and relative EEG power within each of the electrodes continuously or within selected frequency bands, and the symmetry and coherence relationships among these spectral measurements within and between the set of electrodes. This comparison preferably entails transformation of every measure for Gaussianity and rescaling the measure to the common metric of probability by computing the standard or Z score for each variable. A second way to display this data may be as a scrolling waterfall of the Z-transformed spectra or ZSA. A third way to display this QEEG data may be to extract selected, differentially sensitive variables from the EEG and compute separate composites such as Mahalanobis distances or discriminant scores to provide scales which accurately assess DI, PI and MI.

These scores may be displayed as separate, updated numerical values or as separate updated trajectories of the values versus elapsed intra-operative or monitoring time. If the patient begins regaining consciousness, sensitivity to pain or the ability to comprehend speech and store memories, as shown by the trajectory for the corresponding dimension, the confidence level (mean+2 standard deviations) around the self-norm (baseline) for that dimension will be exceeded. An alarm may be sounded or a vibratory signal transmitted. If that occurs, more agent, directed toward the specific dimension displaying change of state, may then be delivered (titrated) to the patient manually by the attending medical personnel or, alternatively, the corresponding agent may be automatically delivered via a self-adaptive servo algorithm. Conversely, if these changes are excessive, less agent will be indicated relative to the self-norm, and the attending personnel or the servo system may reliably intervene to control the administration of each of the agents in a manner optimized for the individual patient.

The QEEG variables may be augmented by sensory evoked potentials ("EPs") and autonomic data to obtain measurements for quantifying the pain (PI) and memory (MI) indices. To obtain the sensory EPs, the system presents to the patient a programmed sequence of concurrent or sequential stimulations in one or multiple sensory modalities. Preferably, two modes are used: (1) auditory stimulation (e.g., auditory clicks or rectangular tone pips at about 65 dB, modulated at a frequency selected to maximize EP amplitude, such as, approximately 1500 Hz), delivered to the ears via air tubes from an audio source at an 'auditory tracer' repetition rate F1; and (2) somatosensory stimulation consisting of electrical shocks (e.g., 0.2 msec pulses of constant current at about 12 mA delivered to a peripheral nerve, preferably via a finger cot, at a second 'somatosensory tracer' rate (F2). The tracer rates F1 and F2, although concurrent, may preferably be selected at different prime number frequencies to permit separation of the different EP's and avoid interference. Concurrent stimulations permit a more rapid, examination and provide the patient's responses more quickly. However, intermittent sequential stimulation may be more effective as habituation may readily be avoided by randomizing sequences or other maneuvers to maximize EP amplitudes. Based an the responses to the auditory stimuli, the system tests the functional state of the lateral lemniscal auditory pathway in the brain stem (Brain Stem Auditory Evoked Response or BAER), the thalamus (Mid-Latency Auditory Evoked Response or MLAER) and the auditory cortex ("AER"). Based on the responses to electrical stimuli, the system tests the functional state of the spinal cord, medial lemniscal pathways in the brain stem and the somatosensory cortex (Somatosensory Evoked Response, or SER).

One way to quantify the EPs is to utilize separate tracer frequencies, F1 and F2, in order detect the different times of presentation of the stimuli in the two different modalities to provide 'trigger pulses' needed to compute the wave shape of each of the average evoked responses in the time domain, using the conventional evoked response averaging techniques. This selective averaging may be performed whether the stimuli are presented simultaneously or sequentially. The raw wave shapes may be optionally displayed as a scrolling waterfall, or Compressed Evoked Potential Array (CEPA). The system may extract from each such wave shape a numerical feature of merit or a metric (e.g., such as the length of the curvilinear outline or the area under the EP wave shape). From a baseline sample for both the AEPs and SEPs, the mean and standard deviation of the distribution of such EP measures may be specified. Subsequent samples may be Z-transformed to provide a common metric of probability. These Z-scores may be displayed as periodically updating numerical values or as continuously updating trajectories. They may also be combined with the Z-scores of the separate QEEG measures found to be sensitive to pain or memory storage into a 'State Vector' in order to provide a multi-modal and more sensitive and specific assessment. Such multivariate vectors may be computed as the square root of the sum of the squared separate Z-scores. Such vectors may combine QEEG and SEP Z-scores to yield a Pain State Vector, QEEG and AEP Z-scores to yield a Memory State Vector, or QEEG, SEP and AEP Z-scores to yield a Brain State Vector.

Another way to quantify the EPs is to perform very narrow band (e.g., using 0.5 Hz frequency bins) FFTs on the EEG recorded in the absence of the tracer stimuli and during intermittent or constant periods of stimulation. Using the very narrow band power computed over a sliding window of appropriate length (e.g., 20 to 60 seconds), the power in the bin corresponding to F1 or F2 is divided by the mean power of the two adjacent bins of lower frequencies and the two adjacent bins of higher frequencies. The power of the EEG is equal to its variance because the variance of a set of samples of a variable equals the mean squared value minus the square of the mean value across the set and the mean value of the EEG is zero. Thus, this quotient of powers is equivalent to an F-ratio. In this way, without actually computing an average response wave shape, a statistically interpretable FIGURE of merit can be readily provided for the responsiveness of the patient to somatosensory or auditory stimulation. By constructing a database of such F values in a baseline sample, the updating F ratio's can be Z-transformed to probability and processed for display on a monitor or inputs to a servo controller just as the features extracted from the EP wave shapes.

Measures of vital signs (e.g., heart rate, stroke volume, blood pressure, respiration and temperature) may also be obtained and monitored from the anesthesiology console. In addition, oxygen saturation may be measured (e.g., using an NIR sensor such as "INVOS"® (In Vitro Optical Spectroscopy). A preferred comprehensive system monitors the electrophysiology of the patient, detecting changes in available measurements of such vital signs. Any such data which becomes available may be treated the same way in principal (i.e., a baseline sample may be collected to serve as the reference state). The quantified feature(s) may then be assembled into a baseline distribution sample. After transforms for Gaussianity, if necessary, the mean and standard deviation of each measure are calculated. Z-transformation of the raw measure values now rescales them all in the common metric of probability. These may now be presented on the screen as numerical values or displayed as continuous updating trajectories as univariates or as multivariate "vital sign vectors" combined by computing the square root of the sum of the squared Z-scores. While a mathematically more correct multivariate may require correction for intercorrelations using the covariance among the set of measures, the simple square root of the sum of squares errs in the direction of possible over-estimation of the vector length, which acts as a 'fail-safe' early warning signal. In particular, the normalized variability in heart rate (HRV) has been reported to be a sensitive autonomic indicator of pain, Z (HRV) might contribute enhanced sensitivity if incorporated into the "pain vector" together with the selected pain-sensitive QEEG variables and selected SEP features.

As shown in FIG. 1, prior to a surgical operation, a plurality of EEG electrodes (e.g., EEG electrodes 2a-2e) are removably secured to the scalp 1 of the patient. Preferably, the EEG electrodes will include the following forehead locations: F1, F2, F7, F8 (all 4 active) and FPZ (reference). The capital letters refer to position location names in the International 10/20 Electrode Placement System as would be understood by those of skill in the art. Additional removable electrodes may be utilized as desired while additional reference electrodes (unilateral or linked) may be removably positioned on the patient's mastoids or earlobes (A1, A2). An electrode may be placed on the shoulder over Erb's Point to serve as confirmation that SEP are being conducted through the spinal cord. EOG electrodes may optionally be placed at the outer canthus of the eye to facilitate artifact rejection. As would further be understood by those of skill in the art, electrodes may also be placed on the central vertex (Cz) to record brainstem potentials, on the chest for EKG recording and on the cheekbone to serve as the ground.

The electrodes 2a-2e preferably use a standard electrolyte gel, or other application method, for contact so that the impedances of each electrode-skin contact are below 5000 ohms. Alternatively, for some applications, needle electrodes, a pre-gelled electrode appliance with adhesive or other means of fixation, or an electrode cap or net with previously located electrode positions may be used. The EEG system, described below, automatically checks the electrode-skin impedance at each electrode at frequent intervals, (e.g., every minute), and displays a warning (e.g., a red LED light) if any such impedance falls below 5000 ohms.

As shown in FIG. 1, the patient's head 1 is connected to the patient module which includes a desired number of electrodes 2a-2e. FIG. 1 shows four active electrodes.

Each of the electrodes 2a-2e is connected to a respective one of the EEG/EP amplifiers 3a-3e, with each electrode lead being connected to its respective amplifier. Each amplifier 3a-3e has an input isolation switch, (e.g., a photo-diode and LED coupler), to prevent current leakage to the patient. The EEG amplifiers 3a-3e are high-gain low-noise amplifiers, preferably having, for example, peak-to-peak noise of 1 microvolt or less, a frequency range of 0.5 to 200 Hz, fixed gain of 10,000, common mode rejection of 100 db or more (4 amplifiers). Two auditory or somatosensory brainstem EP amplifiers may have, for example, a peak to peak noise of less than 1 microvolt, a frequency range from 30 to 5000 Hz, gain of 100,000 (2 amplifiers) and a common mode rejection of at least 100 dB. Alternatively, high-gain amplifiers may be used with fixed gain of, for example, 10,000 of which 2 may be remotely switched to a fixed gain of, for example, 100,000. Amplifier parameters may be switched for separate data collection of EEG and EP, separate amplifiers may be connected to the same electrode input, or a programmable A/D multiplexer converter may be used to output the separated data.

The amplifiers 3a-3e are connected to a four channel analog-to-digital multiplexer 4 (A/D multiplexer). The multiplexer 4 samples the amplified analog brain waves at a rate of, for example, 5 KHz for each channel. The multiplexer 4 is connected to "buffer signal" 5 which stores the signal, and "buffer noise" 6 which stores samples of the "noise", that is, amplifier output of EEG when no stimuli are delivered to elicit EPS. The buffers 5, 6 and A/D multiplexer 4 are connected to a dedicated digital signal processor (DSP) 7, such as, for example, model TMS320C44® (Texas Instruments). Alternatively, the DSP 7 may be a Pentium 4 Processor® (Intel) or a digital signal processor such as the TMS320C44® (Texas Instruments) along with a microprocessor. The DSP may be controlled by, for example, a software program 8 and connected, through a dedicated 512-point FFT 9 (Fast Fourier Transform) to a digital comb filter 10.

The comb filter 10 is connected to, and controls, the IFFT 11 (Inverse Fast Fourier Transform). The output of IFFT 11 is connected to the system microprocessor 12. The microprocessor 12 is also connected to, and controls, the stimulus generator 13 (e.g., lights, loudspeaker, shock, device, etc.), the mass storage 14 (e.g., a hard disk), the display 15 (e.g., a CRT), a printer 16 and a keyboard operator control panel 17. The microprocessor 12 operates under control of a software program 18. Preferably, as shown, the stimulus generator 13 is connected to "auditory" 20, which generates clicks at, for example, 100 dB and at an "auditory tracer" frequency "F1". The clicks may then be transmitted to the patient via, for example, earphones or air tubes. The stimulus generator 13 is also connected to "somatosensory" 21 which delivers electrical stimulation (e.g., constant current electrical shock pulses), for example, of 200 microseconds duration and 12 milliamps current. The electrical stimulation may be transmitted to the patient via, for example, a fingertip cot at a second, and different, "somatosensory tracer" frequency "F2."

The digital comb filter 10 may be as described in U.S. Pat. No. 4,705,049, incorporated by reference herein. The comb filter may considered a series of band pass and band stop filters which are responsive over a selected range. The selected range may for example be is 0-3000 Hz and may, preferably be 0-1400 Hz. Preferably, band pass filters may operate at 10-580 Hz, 600-640 Hz, 720-800 Hz and 900-1400 Hz with band-stop filters at 0-10 Hz, 580-600, 640-720 Hz, 800-900 Hz and above 1400 Hz. Thus the band pass filters form the "teeth" of a comb and are selected to accord with frequencies in which a signal/noise ratio is acceptable. The band-stop filters are selected to remove frequencies in which the noise is excessive.

The multiplexer 4 may be programmed to obtain samples of the signal and of the noise. The "noise" is preferably obtained when there is an absence of evoked potential stimuli and the "signal" is obtained during stimulation, beginning with presentation of the stimuli or after a pre-selected delay. The program 8 with its controlled DSP 7 conditions the input signals and insures that they are valid biological signals. Such validation checks on the input signals include periodic calibration measurements and impedance measurements and continuous automatic artifact rejection algorithms. The microprocessor 12 automatically provides a timed set of two kinds of stimuli for simulator 13: An audio sound from a speaker or earphones and a tactile signal from the electric shock of about 0.2 msec duration and about 12 mA of intensity delivered to electrodes via the fingertip cot. Auditory clicks (e.g., about 100 db SPL) may be delivered through a stethoscope earpiece by air conduction tubes from a magnetic speaker or other arrangement as would be understood by those skilled in the art. Ideally, these clicks may be rectangular pulses of 1500 Hz tones at a repetition rate of about 40/sec. The rate of stimulus may range between 7-50/second and may more preferably range between 35-45/second (i.e., eliciting a 40 Hz auditory steady-state evoked response (40 Hz) at an auditory tracer frequency 1 (F1)).

The patient's brain responds to these stimuli, providing "Evoked Potentials" (EP which are averaged to reduce noise. Sample size varies with stimulus modality, ranging from 100 (VEP) to 512-2048 (BAER/BSER). The average EP is the sum of samples time-locked to the onset of the stimuli divided by the number of samples, to provide an updated average.

The software program provides patient information. Typically, the patient header gives the patient's IDS number, age and the date of the operation. In addition, it may contain the name of the physician, anesthetist or other operator and the nature of the procedure. The time is provided by a time code generator, which records both local time and elapsed time directly on the EEG tracings, so that events may be retrieved from any acquisition session given input to the database of the date. Retrieved data should include all clinical protocols and physiological documentation, including the trajectories of the indices. The software program provides the data analysis module, described in detail elsewhere in this application.

After analysis of the data, the microprocessor 12 provides information to the display 15 which info ns the anesthesiologist or medical personnel of the state of the patient with respect to the 3 dimensions being monitored. This data can then be used to guide manual administration of agents in accordance with the clinical judgment of the physician. Alternatively, this information may be provided as control signals to a delivery control 19, which, automatically controls three agent infusion pumps 22a-22c (e.g., Pumps A, B and C) to achieve a desired balance of the three agents. If the anesthetic is gaseous, the anesthesia control 19 may control valves of gas cylinders (not shown) as would be understood by those of skill in the art.

Each of the three state indices (i.e., the DI, the MI and the PI) are separately analyzed by the computer software of the present invention, in the frequency domain and also in the time domain.

The following is a preferred exemplary method for frequency domain analysis of the depth of anesthesia to obtain the DI. The frequency domain, from 0-200 Hz, is divided into narrow bins (e.g., for 0.50 Hz bins, 400 bins are set), QEEG variables are extracted from 0.05-1.5 Hz (low delta) to gamma 2 (35-50 Hz). Based upon experience (e.g., based on data from sets of prior patients), features are selected from the data from univariate (i.e., single electrode) and multi-variate (i.e., composite sets of electrodes) measures.

The data, in the frequency domain, is preferably converted by a Fast Fourier Transform (FFT) and then may be converted again by an Inverse Fast Fourier Transform (IFFT). The FFT is the preferred method for calculating a power spectrum of the patients' brain waves. Using the Fourier transformation, the complex wave diagram of the EEG is divided into underlying oscillation components, followed by a translation from the time domain into the frequency domain. The squared amplitudes of these oscillation components form the "power spectrum." Further processing of the results of the Fourier analysis may include the extraction of spectrum parameters as well as continued statistical calculations. IFFT may be performed after analysis of the relative phase variances at each frequency, of segments containing EP signals and segments containing only noise samples, removing noise by setting appropriate coefficients to zero and reconstructing EPs with the noise digitally removed. Parameters which may be derived from the spectrum, include, for example, the total power and absolute and relative power in different frequency bands. The median, the spectral edge frequency, and the dominant frequency may also be used as parameters. The median frequency is most often defined as the 95% quantile (i.e., 95% of the total power of the spectrum is below this frequency). The dominant frequency is the frequency with the highest power. Mean powers within selected band intervals are calculated, transformed to achieve a normal or Gaussian distribution. Mean values and standard deviations of a baseline set of samples of each QEEG or EP variable are obtained during an adequate and appropriate reference period to define the patients "self-norm." The relevant population norm is obtained (i.e., from a look-up normative table). Z-scores are calculated for each univariate or multi-variate QEEG or EP measure, relative to both the self- and population-norms. For each variable, a sliding window, for example, 20 seconds of data which is continuously updated, is formed which integrates sequential segments (i.e., 2.5 second artifact-free EEG samples). From the updated mean value of the sliding window, the trajectory of each variable and the DI, PI and MI are calculated. The trajectory of each index is presented to the physician as a quantitative monitor of each dimension of patient state to provide guidance for the optimal management of the patient or optionally may be used to automatically control the delivery of various agents to the patient, preceded or accompanied by display of the intended maneuver to the operator.

The EP wave shapes are stored. The peaks of the EPs are detected and an EP Index ("EPI") is computed. The EPI reflects the area under the EP curve, the length of the contour of the EP wave shape ("string length"), its peak amplitudes and its latencies. An updating EP waterfall type display may be computed (Compressed EP Array, or CEPA), that scrolls (with time) with the EP peaks marked, for example, as brightened points or by arrows or stars. The automatic comb filter, mentioned above, may be used to define an optimum digital filter for computation of any EPs. As in the case of the BAER/AER, for all EPs, the data is stored, the peaks are detected, and an EP Index ("EPI") is computed. The EPI reflects the area under the EP, and its string length, peak amplitudes and latencies. An updating scrolling waterfall display may be computed and displayed (on the monitor) with the EP peaks marked. In addition, separate updated sliding windows of data may be computed and displayed (on the monitor) for the patient's vital signs. Preferably, these vital signs include heart functions, as detected by QRS peaks, heart rate variability, respiratory cycle, BP (Blood Pressure), oxygen saturation, and temperature. These vital signs windows are computed using the means value and standard deviation for each of the vital signs.

The data collected and analyzed in the time domain and frequency domain are used to form the patient's multiple indices. These are, preferably, the Depth Index (PSI) (assesses anesthesia level), the Memory Index (MI) and the Pain Index (PI). A preferred method of computing these indices may be to use discriminant analysis as described in U.S. Pat. No. 5,083,571 relating to psychiatric classification of a patient with respect to a class or specific disorder and the inventor's prior U.S. Pat. No. 6,016,444. In general, discriminant analysis uses "discriminant functions", U.S. Pat. Nos. 5,083,571 and 6,016,444 are hereby expressly incorporated by reference in their entireties.

A discriminant function is composed of weighted combinations of subsets of variables. In the case where patients' norms are used, the subsets are Z scores. Each of the subsets (each Z score) is selected, on the basis of experience and experimentation, because it significantly contributes to the discrimination (e.g., discrimination between anesthetized and yet feeling pain and anesthetized and not feeling pain). The weighting of the subsets, the contribution of each Z score toward the discrimination, is also based on experience and experimentation.

The distributions of features of two groups of subjects, where the groups belong to different diagnostic categories, may be thought of as two clouds of points in a multidimensional space in which each dimension corresponds to a feature. For example, each feature is a Z score and the diagnostic categories, for example, are the degrees of anesthetization to prevent pain. There may be no significant differences between two groups (i.e., significant differences in other dimensions). A problem arises when these clouds of points overlap, i.e., when there is no apparent significant difference between two groups with respect to some features. A solution is to attempt to define a boundary, through the clouds of points, to create a first zone which includes as much as practicable of the first group, and as little as possible of the second group, and a second zone which includes as much as practicable of the second group and as little as practicable of the first group.

The third zone is defined as an overlap region where no reliable classification can be made. In principle, a discriminant function weights the values of selected features for a new patient and adds these weighted values to specify a single point in the relevant multidimensional space. This single point then would be in one of the three zones, and the individual's category (in each of the DI, MI and PI) would be classified accordingly. The discriminant analysis is performed during the operation using Z scores based on self-norms (i.e., comparison with the same patient pre-operation) and population norms (i.e., patients of the same age and condition during similar operations using the same anesthetic). After the DI, MI and PI are computed, these computations may be used to automatically administer the various anesthetics to the patient. In addition, these indices are displayed to the operator on, e.g., a monitor. They may also be recorded and printed out for analysis after the operation. The DI gives an assessment in QEEG, the depth of anesthesia, the Memory Index (MI) is obtained, in QEEG, by combining the F (AER) value with selected AER features (i.e., assessment of reception). This should give an indication of the patients' ability to comprehend speech, i.e., the conversation of the doctors and nurses during the operation. The Pain Index (PI) is derived from the F (SER) values and selected SER features. In addition, non-QEEG autonomic measures, which are responsive to pain, may be used and computed into the PSI, PI and MI.

In order for the tendencies of the DI, MI and PI to control and/or monitor the quantities of the various anesthetics, each of which is primarily directed to one of those indices, it is necessary to measure the effects of those anesthetics on the individual patients. Population norms are based on gender, age, surgical procedure and specific anesthetics. However, individuals, due to their metabolisms and other factors, may react differently from the average patient of such population norms.

The preferred method of determining the correct anesthesia dosage for each patient is to test the patient using the 2 or 3 different anesthetic agents which will be used for the operation. This QEEG method may analyze the particular patient's brain wave reaction to each anesthetic agents, one at a time, and derive a "transfer function" for each patient, reflecting that patient's biochemical reactions to each anesthetic agent. For example, one patient may require an injection of 5 milliliters of an anesthetic agent to prevent a feeling of pain, as shown by his PI, while another patient may require twice that dosage to obtain the same effect. The transfer function is preferably updated at regular intervals (i.e., for example every 20 minutes) during the operation, as it may change if the operation lasts longer than 15-20 minutes.

A preferred method for calculating each of transfer function may include perturbation analysis. After the patient has been anesthetized to the desired plane of anesthesia, and his QEEG self-norm (reference set-point) has been obtained, the system halts delivery of the first anesthetic, for example, the anesthesia remifentanyl primarily directed to control pain (PI) or may diminish the delivered amount by some fraction, for example, 50 percent. The patient then starts, in a gradual way, to show a change in the relevant index, e.g., DI, MI or PI. At a selected distance from a set point, preferably about 2.5 Standard Deviations (S.D.), (i.e., probability $P<0.01$), the application of the particular anesthetic agent is resumed. The system, in this method determines the number of anesthetic units withheld from the patient to cause the change in the relevant index. For example, it may require withholding 3 units for a particular patient to be roused to 2.5 S.D. from the set-point of the PI. The amount of anesthetic agent withheld, called the "test correction amount," is an approximation of the amount of anesthetic agent required to restore that particular patient to the selected index when he has deviated from his set point by 2.5 S.D. A selected fraction of that amount is then administered, as a first approximation, to see whether this restores the patient to the set point. The amount required to restore the patient to the set points is defined as the "correction amount" and is retained in system memory and is administered to the patient whenever the patient has deviated from his set-point by 2.5 S.D. or more.

Adequate determination of the transfer function may require positive, as well as negative perturbations. Preferably, periodic evaluation is shown by a significant change in each index (DI, MI and PI) caused by a small increment in the amount of anesthetic agent delivery, for example 10%.

As shown in FIG. 1, the anesthesia control 19, under management of the microprocessor 12, controls the administration of the different anesthetic agents. In this example, the anesthetic agents are injections and they are administered intravenously by infusion pumps A-C (22a-22c). For example, pump A (22a) may inject propofol (to control DI), while pump B (22b) injects midzolam (to control MI) and pump C (22c) injects remifentanyl (to control PI). Alternatively, as would be understood by those of skill in the art, any or all of the various anesthetic agents may be gases which are administered through controlled inhalation by the patient.

For each index (DI, MI and PI), one infusion pump 22a-22c is used to administer or withhold the anesthetic agent primarily directed toward controlling that index. For example, the DI is continually computed and compared to the desired value or desired range of values. The pump (i.e., pump A (22a)) is energized (or not energized) to inject (or withhold) the corresponding anesthetic agent (e.g., propofol primarily to control the PSI). Similarly, the MI and PT are continually computed and a corresponding one of the pumps 22 (i.e., pump B (22b) or pump C (22c), respectively) is controlled to inject, or withhold, the anesthetic agent primarily directed to that index.

As would be understood by those of skill in the art, the system of FIG. 1 may be implemented incorporating a dedicated freestanding computer, such as a PC, a laptop or other handheld device. Alternatively, the computer and monitor portions (as distinct from the pumps) may be implemented as part of a multi-modal monitor, which may also include sensors and displays of the patient's vital signs (i.e., blood pressure, respiration, O2 saturation, temperature and pulse (heart rate)). In any event, preferably, the display 15 is a monitor having a color screen to display graphics and alphanumerics. The operator control 17 may preferably include a standard ASCI key board which may be used to enter the patient header (e.g., name, age, gender, hospital number, date, medical procedure etc.) and comments (which may use function keys). Preferably, the display shows the results of the QEEG analysis continually during the operation. These displays may preferably include:

a) The trajectories of each of the indices (DI, MI and PI) separately either on the same screen or in sequence;
b) The set points and the selected ranges (permitted deviations) for each index;
c) The current numerical value for each index;
d) A waterfall type display or/and actual (raw data) brain waves showing, for each data channel, the FFT, AER and SER;
e) Coded symbols and/or alarms for events which should be brought to the attention of the operator, such as epileptic spikes, epileptic seizures, burst suppression and abrupt changes in those vital signs (e.g., BP, respiration, pulse (heart rate), O2 saturation and temperature); and
f) Wave shapes stored in an Epileptic form event file (epileptic spikes and seizures) calculated and displayed as well as their number and the their times of occurrences.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining a desired anesthesia dosage for a patient via a perturbation analysis, comprising:
   administering to the patient a first interventional agent at a first rate selected to achieve a first predetermined plane of anesthesia;
   analyzing brain waves of the patient to formulate a first set of data corresponding to a self-norm during administration of the first interventional agent;
   computing from the first set of data a first transfer function corresponding to patient biochemical reactions to the first interventional agent;
   altering the rate of administration of the first interventional agent to the patient by a selected amount after achievement of the first plane of anesthesia for a first time required for the patient to deviate from the first plane of anesthesia by a predetermined degree;
   determining an altered amount of the first interventional agent required to cause the predetermined deviation from the first plane of anesthesia as a difference between an amount of the first interventional agent that would have been delivered to the patient during the first time at the first rate and an amount delivered to the patient during the first time at the altered rate; and
   administering to the patient one of the altered amount of the first interventional agent and a portion of the altered amount of the first interventional agent.

2. The method of claim 1, wherein the alteration corresponds to one of a decrease of the first rate and a termination of the delivery.

3. The method of claim 1, wherein the alteration corresponds to an increase of the first rate.

4. The method of claim 1, further comprising analyzing, at predetermined time intervals, brain waves of the patient to formulate a first further set of data corresponding and computing from the further set of data a first further transfer function corresponding to patient biochemical reactions to the first interventional agent.

5. The method of claim 1, further comprising:
   administering to the patient a second interventional agent at a second rate selected to achieve a second predetermined plane of anesthesia;
   analyzing brain waves of the patient to formulate a second set of data corresponding to a self-norm during administration of the second interventional agent;
   computing from the second set of data a second transfer function corresponding to patient biochemical reactions to the second interventional agent;
   altering the rate of administration of the second interventional agent to the patient by a selected amount after achievement of the second plane of anesthesia for a second time required for the patient to deviate from the second plane of anesthesia by a predetermined degree;
   determining an altered amount of the second interventional agent required to cause the predetermined deviation from the second plane of anesthesia as a difference between an amount of the second interventional agent that would have been delivered to the patient during the second time at the second rate and an amount delivered to the patient during the second time at the altered rate; and administering to the patient one of the altered amount of the second interventional agent and a portion of the altered amount of the second interventional agent.

6. The method of claim 5, wherein the predetermined degree of deviation corresponds to 2.5 standard deviations from the self-norm.

7. The method of claim 5, further comprising analyzing, at predetermined time intervals, brain waves of the patient to formulate a second further set of data corresponding and computing from the further set of data a second further transfer function corresponding to patient biochemical reactions to the second interventional agent.

8. The method of claim 1, further comprising the step of controlling a pump to one of increase and decrease a supply of the first interventional agent to the patient.

9. The method of claim 5, wherein the first predetermined plane of anesthesia is in a first one of a Depth Index (DI), a Memory Index (MI) and a Pain Index (PI), wherein the DI corresponds to a depth of anesthesia of the patient, the PI corresponds to a sensitivity of the patient to pain and the MI corresponds to an ability of the patient to form and store memories.

10. The method of claim 9, wherein the second predetermined plane of anesthesia is in a second of the DI, MI and PI.

11. A method of determining a desired anesthesia dosage for a patient comprising:
    administering to the patient a first interventional agent at a first rate selected to achieve a first plane of anesthesia;
    receiving data from the patient corresponding to the first plane of anesthesia of the patient;
    altering, after the patient has achieved the first plane of anesthesia, a rate of delivery of the first interventional agent to an altered rate for a first time required for the patient to deviate from the first plane of anesthesia by a predetermined degree;
    determining an altered amount of the first interventional agent required to cause the predetermined deviation from the first plane of anesthesia as a difference between an amount of the first interventional agent that would have been delivered to the patient during the first time at the first rate and an amount delivered to the patient during the first time at the altered rate; and
    administering to the patient one of the altered amount of the first interventional agent and a portion of the altered amount of the first interventional agent.

12. The method of claim 11, wherein the data corresponds to brain waves of the patient.

13. The method of claim 12, wherein the first predetermined plane of anesthesia is in a first one of a Depth Index (DI), a Memory Index (MI) and a Pain Index (PI), wherein the DI corresponds to a depth of anesthesia of the patient, the PI corresponds to a sensitivity of the patient to pain and the MI corresponds to an ability of the patient to form and store memories.

* * * * *